US010925745B2

(12) United States Patent
Cardon et al.

(10) Patent No.: US 10,925,745 B2
(45) Date of Patent: Feb. 23, 2021

(54) GLENOID IMPLANT FOR A SHOULDER PROSTHESIS, AND SET FOR ASSEMBLING SUCH A GLENOID IMPLANT

(71) Applicant: Tornier, Montbonnot-Saint-Martin (FR)

(72) Inventors: Jean-Emmanuel Cardon, Domene (FR); Christophe Magnac, Revel (FR)

(73) Assignee: Tornier, Montbonnot-Saint-Martin (FR)

( * ) Notice: Subject to any disclaimer, the term of this patent is extended or adjusted under 35 U.S.C. 154(b) by 148 days.

(21) Appl. No.: 15/828,953

(22) Filed: Dec. 1, 2017

(65) Prior Publication Data

US 2018/0161169 A1    Jun. 14, 2018

(30) Foreign Application Priority Data

Dec. 9, 2016   (EP) ..................................... 16306650

(51) Int. Cl.
*A61F 2/40*        (2006.01)
*A61F 2/46*        (2006.01)
(Continued)

(52) U.S. Cl.
CPC .......... *A61F 2/4081* (2013.01); *A61F 2/4637* (2013.01); *A61B 17/86* (2013.01);
(Continued)

(58) Field of Classification Search
CPC .. A61F 2/40; A61F 2/4081; A61F 2/34; A61F 2002/3401–3495; A61F 2/36;
(Continued)

(56) References Cited

U.S. PATENT DOCUMENTS 4,227,265 A    10/1980 Frey
4,995,883 A    2/1991 Demane et al.
(Continued)

FOREIGN PATENT DOCUMENTS

DE    102014206695    10/2014
EP      1 607 070     12/2005
(Continued)

OTHER PUBLICATIONS

European Search Report issued in EP Application No. 16306650.9, dated Jun. 1, 2017, in 7 pages.

*Primary Examiner* — Brian A Dukert
*Assistant Examiner* — Rebecca Lynee Zimmerman
(74) *Attorney, Agent, or Firm* — Knobbe Martens Olson & Bear, LLP (57) ABSTRACT

The glenoid implant comprises a baseplate, an articular component which has a convex articular surface, and a platform which is provided both to be secured to the articular component by a first attachment and to be secured to the baseplate by a second attachment, the first attachment being independent from the second attachment and defining an assembly axis along which the platform and the articular component are assembled together. The first attachment comprises both a translational connection that is intraoperatively operable to prevent translation between the platform and the articular component along the assembly axis, and a rotational connection that is intraoperatively operable to prevent rotation between the platform and the articular component around the assembly axis, the translational connection and the rotational connection being distinct from each other. The glenoid implant allows assembling the platform indifferently with one of various articular components which differ from each other for example by their material composition and/or by some geometric features of their convex articular surface and/or etc. The articular com- (Continued)

ponent that is effectively assembled with the platform can be chosen by the surgeon during surgery, i.e. during an implantation operation or just before the latter.

19 Claims, 8 Drawing Sheets

(51) Int. Cl.
 *A61F 2/30* (2006.01)
 *A61B 17/86* (2006.01)
(52) U.S. Cl.
 CPC ......... *A61F 2/30749* (2013.01); *A61F 2/4612* (2013.01); *A61F 2002/305* (2013.01); *A61F 2002/3065* (2013.01); *A61F 2002/30329* (2013.01); *A61F 2002/30332* (2013.01); *A61F 2002/30367* (2013.01); *A61F 2002/30405* (2013.01); *A61F 2002/30484* (2013.01); *A61F 2002/30485* (2013.01); *A61F 2002/30507* (2013.01); *A61F 2002/30528* (2013.01); *A61F 2002/30574* (2013.01); *A61F 2002/30604* (2013.01); *A61F 2002/30607* (2013.01); *A61F 2002/30616* (2013.01); *A61F 2002/30772* (2013.01); *A61F 2002/30822* (2013.01); *A61F 2002/30878* (2013.01); *A61F 2002/4085* (2013.01); *A61F 2002/4628* (2013.01); *A61F 2002/4638* (2013.01); *A61F 2002/4641* (2013.01)
(58) Field of Classification Search
 CPC .. A61F 2002/30383; A61F 2002/30485; A61F 2002/30494; A61F 2002/305; A61F 2002/30574; A61F 2002/30576; A61F 2002/30822; A61F 2002/30484
 See application file for complete search history.

(56) References Cited

U.S. PATENT DOCUMENTS

| | | | |
|---|---|---|---|
| 5,741,335 | A | 4/1998 | Gerber et al. |
| 6,679,916 | B1 | 1/2004 | Frankle et al. |
| 6,736,851 | B2 | 5/2004 | Maroney et al. |
| 7,303,585 | B2 | 12/2007 | Horber |
| 8,246,687 | B2 | 8/2012 | Katrana et al. |
| 8,308,812 | B2 * | 11/2012 | Kellar ................ A61F 2/30767 623/18.11 |
| 8,821,503 | B2 | 9/2014 | Tornier et al. |
| 8,945,229 | B2 | 2/2015 | Lappin |
| 2004/0059429 | A1 * | 3/2004 | Amin .................... A61F 2/3609 623/23.51 |
| 2009/0281631 | A1 | 11/2009 | Naidu |
| 2010/0161072 | A1 * | 6/2010 | Drescher ................ A61F 2/34 623/22.29 |
| 2016/0030180 | A1 * | 2/2016 | Wecker ................... A61F 2/30 623/18.11 |
| 2017/0100251 | A1 * | 4/2017 | Ek ............................ A61F 2/30 |

FOREIGN PATENT DOCUMENTS

| | | |
|---|---|---|
| EP | 1 639 967 | 3/2006 |
| EP | 1 782 764 | 5/2007 |
| EP | 1 980 221 | 10/2008 |
| FR | 2 261 743 | 9/1975 |
| FR | 2 310 120 | 12/1976 |
| FR | 2 832 625 | 5/2003 |
| WO | WO 2012/125795 | 9/2012 |
| WO | WO 2014/166877 | 10/2014 |

* cited by examiner

GLENOID IMPLANT FOR A SHOULDER PROSTHESIS, AND SET FOR ASSEMBLING SUCH A GLENOID IMPLANT

The present invention concerns a glenoid implant for a shoulder prosthesis. The invention also concerns a set for assembling such a glenoid implant.

In a healthy human shoulder, the head of the humerus, which is generally ball-shaped, and the glenoid cavity of the scapula, articulate with each other and form a ball-and-socket joint. Total shoulder arthroplasty is a common treatment for shoulder pain resulting from arthritis or injury and leads to replace the ball-and-socket joint by a shoulder orthopedic prosthesis comprising both a glenoid implant to be implanted on the glenoid of the scapula and a humeral implant to be implanted on the humerus. A shoulder prosthesis is considered as being anatomic when the glenoid implant has a concave articulating surface with which a complementary convex surface of the humeral implant articulates. A shoulder prosthesis is considered as being reversed when the glenoid implant has a convex articulating surface with which a complementary concave surface of the humeral implant articulates, the natural anatomy of the ball-and-socket joint of the shoulder thus being reversed. The invention focuses on glenoid implants for reversed shoulder prosthesis.

Each of US 2016/0030180 and U.S. Pat. No. 8,246,687 discloses a modular glenoid implant which comprises a baseplate, a convex articular component and a platform that is interposed between the baseplate and the articular component so as to secure the articular component to the baseplate. In both cases, the articular component is secured to the platform by an attachment implemented in factory: in US 2016/0030180, the factory attachment is achieved by conical clamping, the articular component being necessarily made of ceramic; in U.S. Pat. No. 8,246,687, the factory attachment is achieved by molding, the articular component being necessarily polymeric. These attachments are efficient and safe, in the sense that their factory implementation is provided to achieve higher connecting forces, without risk of intraoperative contamination. However, they raise economic and practical problems. In particular, insofar as for a given patient, the surgeon needs to choose the reversed glenoid implant which is the most suitable to the patient in terms of size and geometry, such factory assembled modules including the articular component and the platform need to be available to the surgeon in various sizes and geometries, which induces substantial inventory constraints.

One of the goals of the present invention is to overcome at least some of the afore-mentioned problems, especially the constraints related to inventories of the various pieces used to provide a modular glenoid implant.

To this end, one object of the invention is a glenoid implant for a shoulder prosthesis, comprising a baseplate, an articular component which has a convex articular surface, and a platform which is provided both to be secured to the articular component by a first attachment and to be secured to the baseplate by a second attachment, the first attachment being independent from the second attachment. The first attachment defines an assembly axis which extends in a proximodistal direction and along which the platform and the articular component are assembled together. Moreover, the first attachment comprise both a translational connection that is intraoperatively operable to prevent translation between the platform and the articular component along the assembly axis and a rotational connection that is intraoperatively operable to prevent rotation between the platform and the articular component around the assembly axis, the translational connection and the rotational connection being distinct from each other.

The glenoid implant according to the invention allows assembling the platform indifferently with one of various articular components which differ from each other for example by their material composition and/or by some geometric features of their convex articular surface and/or etc. The articular component that is effectively assembled with the platform can be chosen by the surgeon during surgery, i.e. during an implantation operation or just before the latter: indeed, thanks to the invention, the chosen articular component is designed to be intraoperatively assembled with the platform so as to be efficiently secured with the platform, especially both in translation along an assembly axis and in rotation around this assembly axis.

Another object of the invention is a set for assembling a glenoid implant, comprising a baseplate, at least two articular components, each of the at least two articular components having a convex articular surface, and a platform which is provided both to be secured selectively to the at least two articular components by a first attachment and to be secured to the baseplate by a second attachment, the first attachment being independent from the second attachment. The first attachment defines an assembly axis which extends in a proximodistal direction and along which the platform is assembled selectively with the at least two articular components. The first attachment comprises a translational connection that is intraoperatively operable to prevent translation between the platform and the selected articular component along the assembly axis, and a rotational connection that is intraoperatively operable to prevent rotation between the platform and the selected articular component around the assembly axis, the translational connection and the rotational connection being distinct from each other.

According to additional advantageous features of the glenoid implant and of the set:
  the translational connection includes at least one translational stop feature of the platform and at least one translational stop feature of the articular component, which are designed to be intraoperatively engaged together and, when engaged together, to mechanically interfere with each other so as to prevent translation between the platform and the articular component along the assembly axis;
  the at least one translational stop feature of the platform comprises at least one flange that is elastically deformable with respect to the rest of the platform, and wherein the at least one translational stop feature of the articular component comprises at least one recess, into which the at least one flange is snapped after being elastically deformed upon intraoperative assembly between the platform and the articular component, and with which the at least one flange axially interferes to prevent translation along the assembly axis in an axial direction in which the platform and the articular component move away from each other;
  the platform comprises a proximal top, a distal base and an intermediate part between the proximal top and the distal base, the intermediate part including at least one wall which rigidly connects the proximal top and the distal base, and the at least one flange, the at least one wall and the at least one flange being arranged in turn around the assembly axis;
  the at least one translational stop feature of the platform comprises at least one abutment surface, and the at least one translational stop feature of the articular component comprises at least one bearing surface which is axially supported against the at least one abutment surface to prevent translation along the assembly axis in an axial direction in which the platform and the articular component move toward each other;

the at least one bearing surface of the articular component is concave and is defined into a socket of the articular component, the socket being axially opposed to the convex articular surface of the articular component, and the at least one abutment surface of the platform is convex and is defined by a part of the platform, which is housed within the socket when the platform and the articular component are assembled together;

the part of the platform, which defines the at least one abutment surface and which is housed within the socket when the platform and the articular component are assembled together, includes the proximal top and/or the at least one wall of the intermediate part;

the at least one bearing surface of the articular component is planar perpendicularly to the assembly axis and is defined by an edge of the articular component, the edge bordering the convex articular surface of the articular component, and the at least one abutment surface of the platform is planar perpendicularly to the assembly axis and is defined by a collar of the platform, the collar being located against the edge of the articular component when the platform and the articular component are assembled together;

the rotational connection includes at least one rotation stop feature of the platform and at least one rotation stop feature of the articular component, which are designed to be intraoperatively engaged together and, when engaged together, to mechanically interfere with each other so as to prevent rotation between the platform and the articular component around the assembly axis;

the at least one rotation stop feature of the platform comprises at least one projection that is arranged radially to the assembly axis, and wherein the at least one rotation stop feature of the articular component comprises at least one notch with which the at least one projection orthoradially interferes to prevent rotation around the assembly axis;

the at least one projection is carried by the at least one wall of the intermediate part;

the at least one projection and the at least one notch are designed to interfere together to prevent rotation around the assembly axis in both directions of rotation.

the at least one notch is cut into the articular component by the at least one projection upon intraoperative assembly between the platform and the articular component;

the second attachment comprises a taper connection between the platform and the baseplate and a locking member extending between the platform and the baseplate, the taper connection and the locking member being intraoperatively operable to fixedly secure the platform and the baseplate together;

the platform has a dome shape which is centered on the assembly axis;

the set further comprises a tool for counteracting the first attachment between the platform and at least one of the at least two articular components;

at least one of the at least two articular components has at least one through-hole which opens on the at least one flange of the platform when the platform and the corresponding articular component are assembled together, and the tool is designed to be introduced into the at least one trough-hole and to act on the at least one flange to deform the at least one flange so that the at least one flange does not interfere anymore with the recess;

the at least two articular components are made in respective material compositions which are different;

each of the material compositions is selected from a group including a polymeric material, a metal material and a ceramic;

the at least two articular components differ from each other by at least one geometric feature of their respective convex articular surface;

each of the respective convex articular surfaces of the at least two articular components defines a central axis which, when the corresponding articular component of the at least two articular components is assembled with the platform, is both parallel to the assembly axis and laterally offset from the assembly axis with an offset value that is possibly null, the offset values respectively associated to the at least two articular components being different.

Embodiments of the invention will be better understood from reading the description which will follow, which is given solely by way of example and with reference to the drawings in which.

Figure 1:
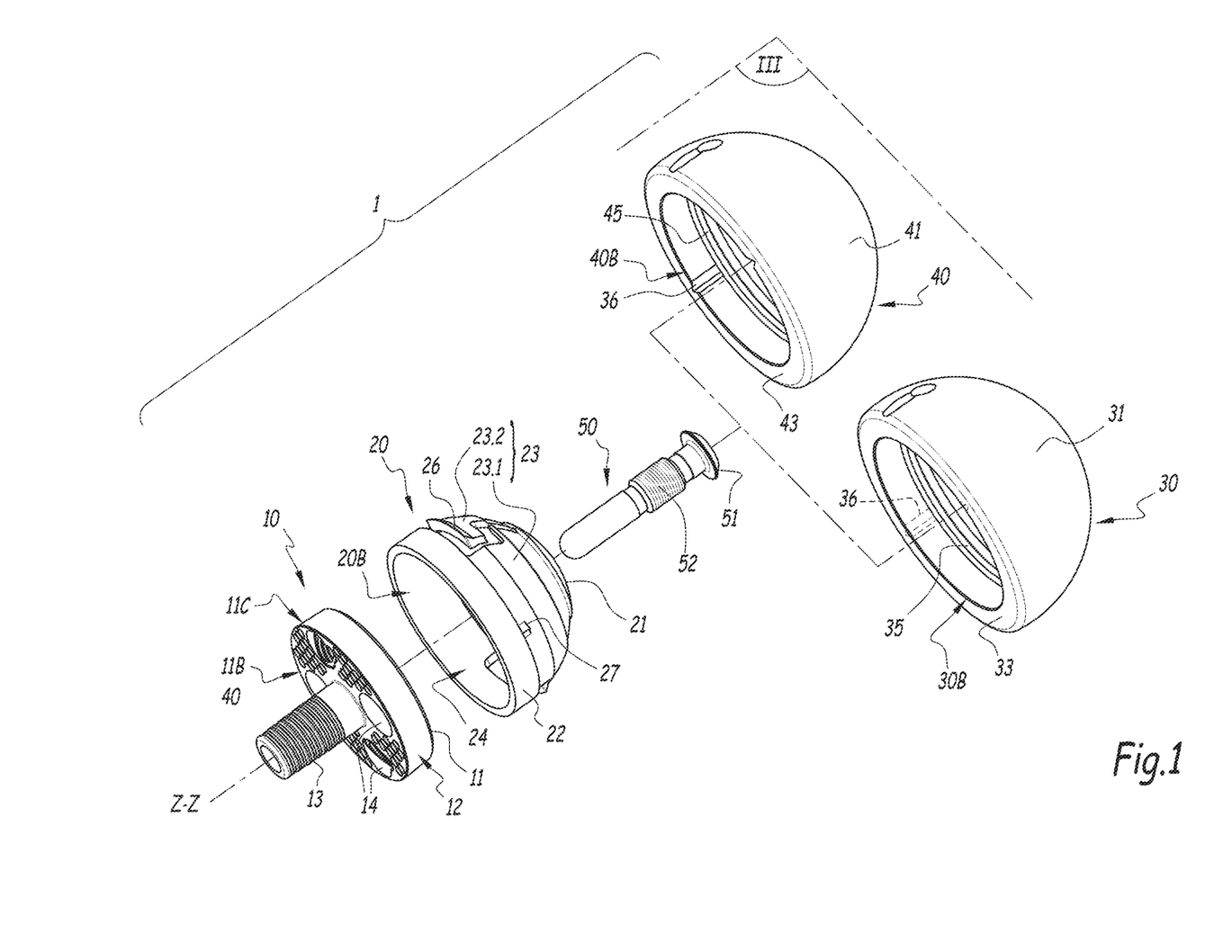
FIG. 1 is an exploded perspective view of a set for a glenoid implant.
Figure 2:
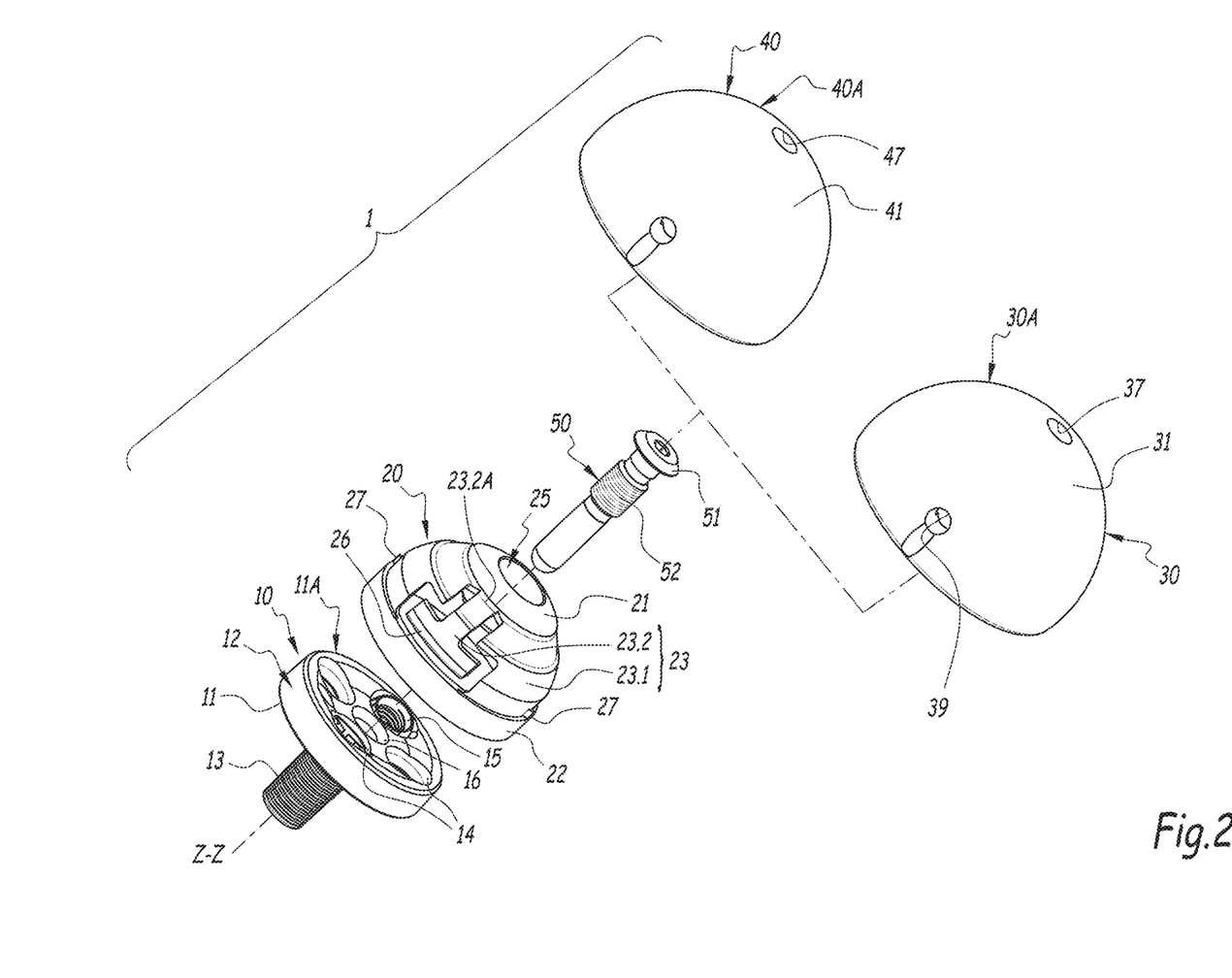
FIG. 2 is a view similar to FIG. 1, having a different angle of observation.
Figure 3:
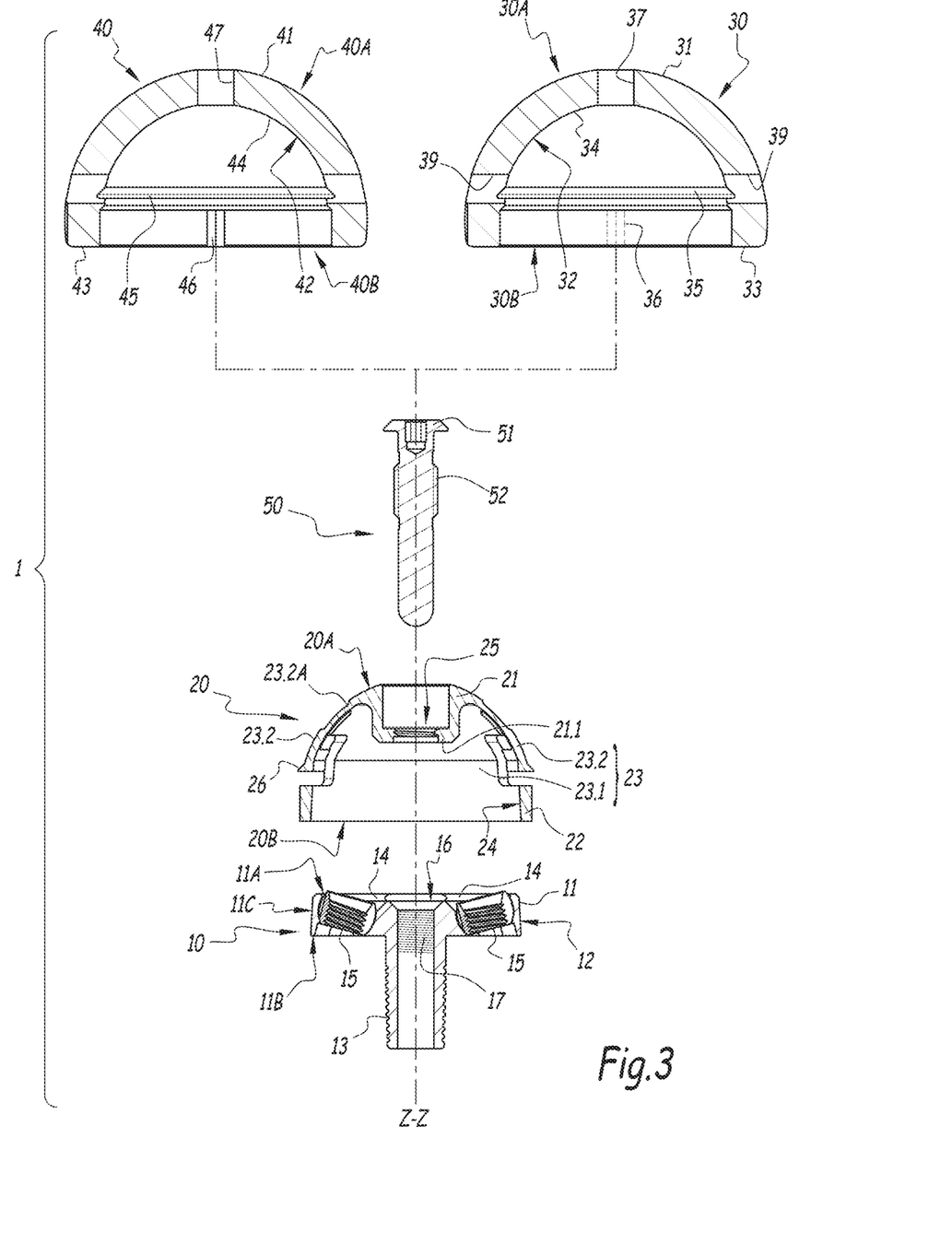
FIG. 3 is a cross-sectional view in the plane III of FIG. 1.
Figure 4:
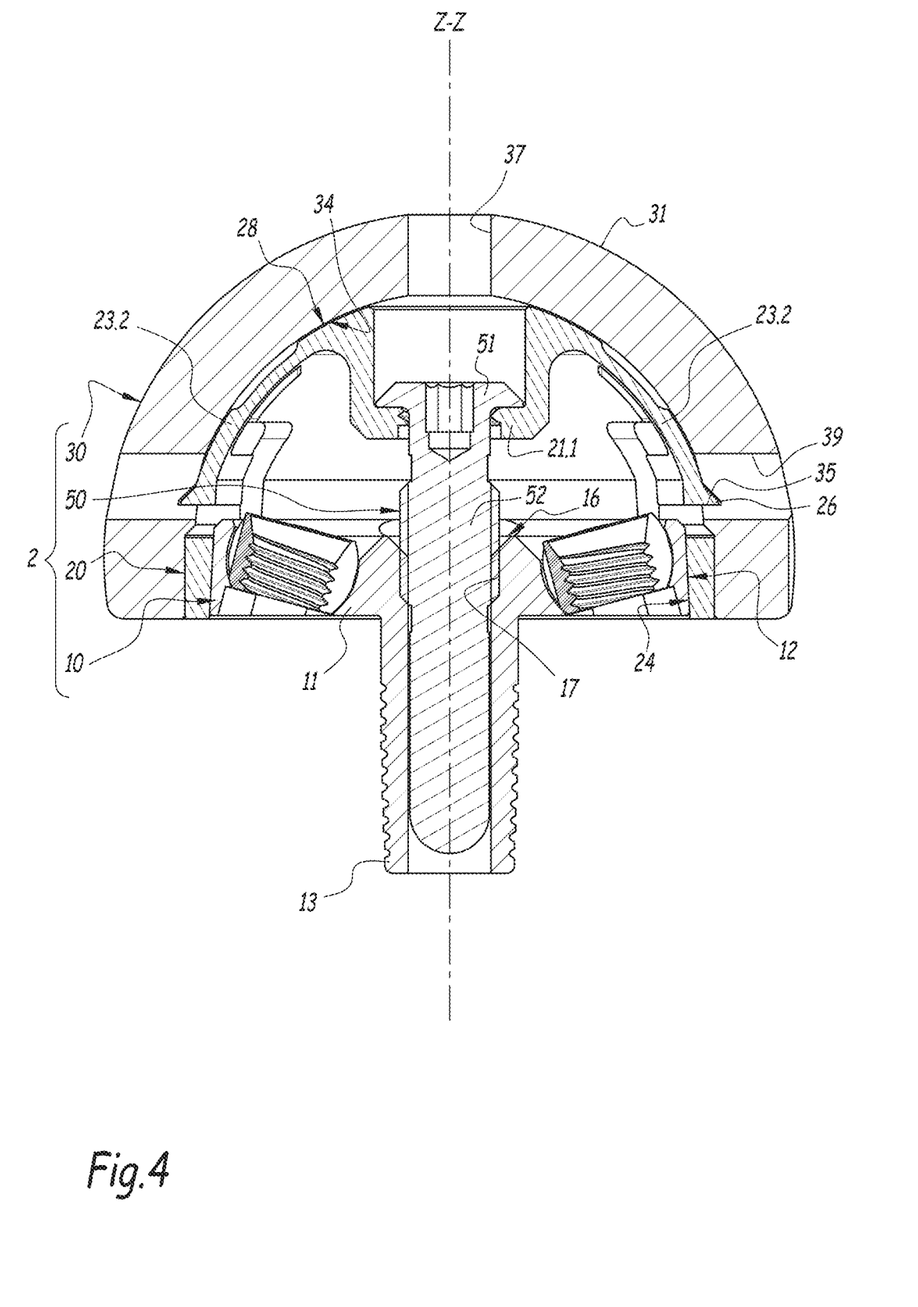
FIG. 4 is a cross-sectional view in the same plane of FIG. 3, illustrating an assembled glenoid implant obtained from the set of claim 1.
Figure 5:
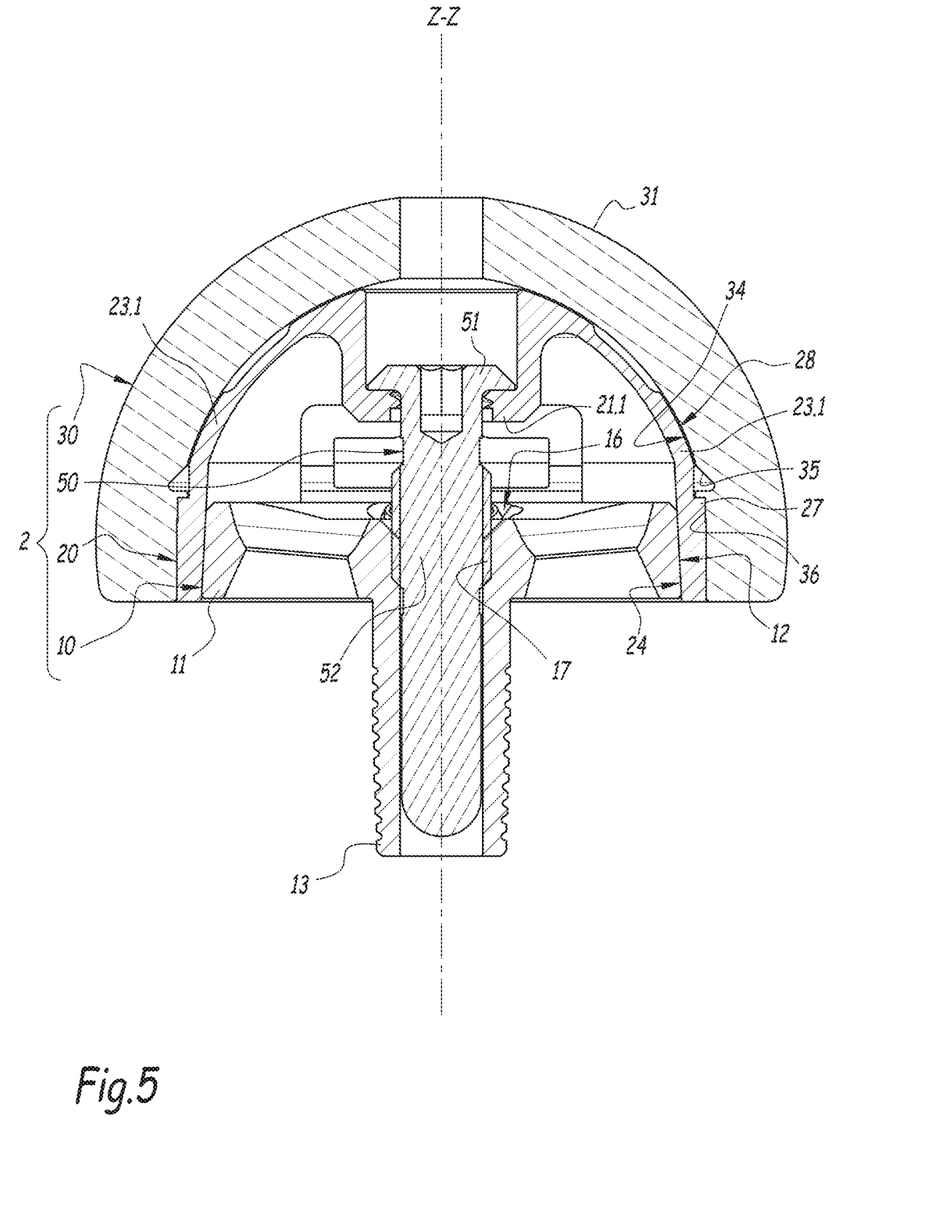
FIG. 5 is a view similar to FIG. 4 in a plane perpendicular to the cross-sectional plane of FIG. 4.

The FIGS. 1 to 3 show a set 1 of prosthetic components from which a glenoid implant can be obtained by assembling at least some of these components along an assembly axis Z-Z. The assembly axis Z-Z is considered as extending in a proximodistal direction. In some embodiments as the one shown in the FIGS. 1 to 3, the set 1 comprises a baseplate 10, a platform 20, a first articular component 30 and a second articular component 40. It should be understood that while both the first articular component 30 and the second articular component 40 may be provided, the baseplate and platform will connect to either the first or second articular component. The FIGS. 4 and 5 show a glenoid implant 2 which is obtained by assembling the baseplate 10, the platform 20 and the first articular component 30 together. Another glenoid implant (not shown) can be obtained by assembling the baseplate 10, the platform 20 and the second articular component 40. The components 10, 20, 30 and 40 are further described in turn below.

The baseplate 10 is intended to be secured to a human glenoid. For this purpose, the baseplate 10 includes a body 11 which is adapted to be secured to the glenoid of a human patient. The body 11 has two opposed faces, i.e. a proximal face 11A and a distal face 11B, which extend transversely to the assembly axis Z-Z. The body 11 is thus arranged across the assembly axis Z-Z. In some embodiments as the one shown in the figures, the proximal face 11A and the distal face 11B are essentially planar and extend perpendicularly to the assembly axis Z-Z. The body 11 further defines a peripheral face or edge 110 which links the proximal face 11A and the distal face 11B to each other at the periphery of the body 11. In some embodiments as the one shown in the figures, the body 11 is centered on the assembly axis Z-Z and has a discoid shape that is centered on this axis, the peripheral face 110 having a circular profile.

For reasons that are explained later, the peripheral face 11C includes or even consists of a frustoconical surface 12 that is convergent toward the proximal face 11A. In some embodiments as the one shown in the figures, the frustoconical surface 12 is centered on the assembly axis Z-Z.

The body 11 is provided with arrangements designed to enable to anchor the baseplate 10 into the glenoid. In practice, the embodiments of these arrangements are not limitative for the invention. In some embodiments as the one shown in the figures, these arrangements include a keel 13, which projects from the distal face 11B of the body 11 and which is centered on the assembly axis Z-Z: this keel 13 is intended to be fitted in a complementary hole of the glenoid which may be preprepared accordingly. Furthermore, in some embodiments as the one shown in the figures, the aforesaid arrangements include through-holes 14, which link each the proximal face 11A and the distal face 11B to each other and which are distributed around the assembly axis Z-Z: each of these through-holes 14 is intended to receive a screw (not shown) for anchoring into the glenoid, being noticed that a split sleeve 15 may be interposed between the screw and the wall of the through-hole so as to adjust the tilt of the screw with respect to the through-hole.

For reasons that are explained later, the body 11 is further provided with a central bore 16, which opens onto the proximal face 11A and which has a threaded 17 portion. In some embodiments as the one shown in the figures, the central bore 16 is centered on the assembly axis Z-Z and extends distally within the keel 13.

The platform 20 has two faces, i.e. a proximal face 20A and a distal face 20B, which are opposed each other in the direction of the assembly axis Z.Z. The distal face 20B of the platform 20 is turned towards the proximal face 11A of the baseplate 10 when the platform and the baseplate are assembled together. In some embodiments as the one shown in the figures, the proximal face 20A and the distal face 20B of the platform 20 are both centered on the assembly axis Z-Z and the proximal face 20A is convex whereas the distal face 20B is concave. Thus, the platform 20 has a dome shape that is centered on the assembly axis Z-Z.

In its proximal part, the platform 20 forms a top 21. In its distal part, the platform 20 forms a base 22. Between the top 21 and the base 22, the platform 20 forms an intermediate part 23.

The base 22 is provided internally with a frustoconical surface 24 belonging to the distal face 20B. The frustoconical surface 24 is convergent toward the intermediate part 23 and is complementary to the frustoconical surface 12 of the baseplate 10. Upon assembling of the baseplate 10 and the platform 20, the body 11 is arranged inside the base 22 as shown in the FIGS. 4 and 5, so that the frustoconical surfaces 12 and 24 engage together so as to form a taper connection, especially a Morse taper connection, between the baseplate 10 and the platform 20.

The top 21 of the platform 20 is provided with a through-hole 25 which links the proximal face 20A and the distal face 20B one to the other. In some embodiments as the one shown in the figures, the through-hole 25 is centered on the assembly axis Z-Z. The through-hole 25 is bounded by a rim 21.1 belonging to the top 21. Upon the assembly between the baseplate 10 and the platform 20, a locking member 50 of the set 1 is added into the through-hole 25, being introduced therein from the proximal face 20A of the platform 20. The locking member 50 is designed to extend between the platform 20 and the baseplate 10, a head 51 of this locking member resting against the rim 21.1 while a threaded rod 52 of this locking member is coaxially received in the central bore 16, being screwed into the thread 17 thereof.

Based on the foregoing, it will be understood that the taper connection, that is formed by the engaged frustoconical surfaces 12 and 24, and the locking member 50 are operable to fixedly secure the baseplate 10 and the platform 20 together. In this way, this taper connection and this locking member form at least partly a platform-baseplate attachment which is designed to secure the baseplate and the platform one to the other. Of course, other embodiments are possible for this platform-baseplate attachment, provided this attachment is operable intraoperatively, that is to say operable by a surgeon during surgery, i.e. in the course of a surgical procedure for implanting in a patient a glenoid implant from the set 1.

Returning to the description of the platform 20, the intermediate part 23 thereof includes at least one wall 23.1 which rigidly connects the top 21 and the base 22 so as to transmit forces between the top 21 and the base 22, including the forces resulting from the engagement of the locking member 50 between the platform 20 and the baseplate 10. In some embodiments as the one shown in the figures, two such walls 23.1 are provided being diametrically opposed with respect to the assembly axis Z-Z. For reasons that are explained later, the intermediate part 23 further includes at least one flange 23.2 that is elastically deformable with respect to the rest of the platform 20. In some embodiments as the one shown in the figures, two such flanges 23.2 are provided, being diametrically opposed with respect to the assembly axis Z-Z. More generally, the wall(s) 23.1 and the flange(s) 23.2 of the intermediate part 23 are arranged in turn around the assembly axis Z-Z. Whatever the number of the flange(s) 23.2, each of them is separated from the rest of the platform 20, except at an end 23.2A of the flange where the flange is deformably joined to the rest of the platform 20: by deformation of this end 23.2A, the flange 23.2 is movable from a rest position, which is shown in the figures and in which the curvature of the flange is identical to the curvature of the wall(s) 23.1, to a deformed position (not shown) in which the curvature of the flange is modified. In use, each of the flanges 23.2 moves from its rest position to its deformed position by application of an external force, whereas the flange moves from its deformed position to its rest position by elastic return. In some embodiments as the one shown in the figures, the end 23.2A of each flange 23.2 is located at the proximal side of the flange and connects the rest of the flange to the top 21 of the platform 20. Moreover, each of the flanges 23.2 is provided externally with a projection 26 that is designed to be projecting from the rest of the proximal face 20A of the platform 20 when the flange is in its rest position. In some embodiments as the one shown in the figures, the projection 26 of each flange 23.2 is located at the distal side of the flange and has an elongated shape running around the assembly axis Z-Z.

Also for reasons that are explained later, the platform 20 is provided externally with at least one projection 27, which is designed to be projecting from the rest of the proximal face 20A of the platform and which is arranged radially to the assembly axis Z-Z. In some embodiments as the one shown in the figures, two such projections 27 are provided, being diametrically opposed with respect to the assembly axis Z-Z, and are respectively carried by the walls 23.1 of the intermediate part 23.

Each of the first and second articular components 30 and 40 has two faces, i.e. a proximal face 30A, 40A and a distal face 30B, 40B, which are opposed each other in the direction of the assembly axis Z-Z. The distal face 30B, 40B of the articular component 30, 40 is turned towards the proximal face 20A of the platform 20 when the articular component and the platform are assembled together. The proximal face 30A, 40A is at least partly or even totally convex, so as to include a convex articular surface 31, 41 that is intended to articulate with a complementary concave surface of a humeral implant. In some embodiments as the one shown in the figures, the distal face 30B, 40B of each of the first and second articular components 30 and 40 is at least partly concave and thus includes a socket 32, 42 that is linked to the convex articular surface 31, 41 by an edge 33, 43 of the articular component 30, 40. In some embodiments as the one shown in the figures, the socket 32, 42 and the edge 33, 43 are each centered on the assembly axis Z-Z.

As indicated above, each of the first and second articular components 30 and 40 can separately be assembled with the platform 20 by means of dedicated arrangements which are detailed here-after. In some embodiments as the one considered in the FIGS. 1 to 3, the first articular component 30 and the second articular component 40 differ from each other within the set 1 by their respective material composition. In practice, each of these material compositions is selected from a group including a polymeric material, including polyethylene and polymer mixtures or copolymers of polyethylene, a metal material, including various metal alloys, and a ceramic, including pyrocarbon and various other ceramics. By way of example for the rest of the description, it can be considered that the articular component 30 is made of polyethylene and the articular component 40 is made of pyrocarbon or a metal alloy.

The socket 32, 42 of each of the articular components 30 and 40 defines a concave bearing surface 34, 44 which is designed to, upon the assembly of the articular component 30, 40 with the platform 20, to be supported against a convex abutment surface 28 of the platform in the direction of the assembly axis Z-Z, this abutment surface 28 being defined by a part of the platform that is housed within the socket 32 when the platform and the articular component are assembled together. In the embodiment of the FIGS. 1 to 5, the aforesaid convex abutment surface 28 is defined by the top 21 and/or the walls 23.1 of the intermediate part 23 of the platform 20, as indicated in FIGS. 4 and 5. When the bearing surface 34, 44 of the articular component 30, 40 and the abutment surface 28 of the platform 20 are axially supported one against the other, as shown in the FIGS. 4 and 5 for the articular component 30, these bearing and abutment surfaces prevent translation along the assembly axis Z-Z in a direction in which the platform and the articular component move toward each other. Thus, the abutment surface 28 and the bearing surface 34, 44 respectively form at least partly first translational stop features of the platform 20 and of the articular component 30, 40, which are designed to be engaged together and, when engaged together, to mechanically interfere with each other so as to prevent translation between the platform and the articular component along the assembly axis Z-Z in the axial direction in which the platform and the articular component move toward each other. The embodiments of these first translational stop features, such as the abutment surface 28 and the bearing surface 34, 44, are not limitative, provided the engagement of these first translational stop features together is operable intraoperatively, that is to say operable by a surgeon during surgery, i.e. in the course of a surgical procedure for implanting in a patient a glenoid implant from the set 1.

The socket 32, 42 of the articular component 30, 40 is further provided internally with a recess 35, 45. In some embodiments as the one shown in the FIGS. 1 to 5, the recess 35, 45 comprises or even consists of a groove which runs continuously in a peripheral direction around the assembly axis Z-Z. The recess 35, 45 is designed to receive the projection 26 of the flange(s) 23.2 of the platform 20 when the flange is in its rest position. Upon the assembly between the platform 20 and the articular component 30, 40, the projection 26 of the flange(s) 23.2 is snapped into the recess 35, 45 after the flange is successively deformed from its rest position to its deformed position by pinching the flange toward the assembly axis Z-Z, then again deformed from its deformed position to its rest position by elastic return. The aforesaid pinching of the flange(s) 23.2 may result from the axial introduction of the intermediate part 23 of the platform into the distal end of the socket 32, 42. When the flange(s) 23.2 is thus snapped into the recess 35, 45, the projection 26 of the flange axially interferes with the recess 35, 45 to prevent translation between the platform 20 and the articular component 30, 40 along the assembly axis Z-Z in a direction in which the platform and the articular component move away from each other. Thus, the flange(s) 23.2 and the recess 35, 45 respectively form at least partly second translational stop features of the platform 20 and of the articular component 30, 40, which are designed, upon the assembly between the platform and the articular component, to mechanically interfere with each other so as to prevent translation between the platform and the articular component along the assembly axis Z-Z in the axial direction in which the platform and the articular component move away from each other. In practice, the embodiments of these second translational stop features, such as the flanges 23.2 and the recess 35, 45, are not limitative, provided that the engagement of these second translation stop features together is operable intraoperatively, that is to say is operable by a surgeon during surgery, i.e. in the course of a surgical procedure for implanting in a patient a glenoid implant from the set 1.

Based on the foregoing, it will be understood that the aforesaid first translational stop features and second translational stop features of the platform 20 and of each of the articular components 30 and 40 form at least partly a translational connection for securing the platform and the articular component one to the other upon the assembly thereof, this translation connection being intraoperatively operable to prevent translation between the platform and the articular component along the assembly axis Z-Z in both directions of this assembly axis.

Furthermore, each of the articular components 30 and 40 is provided with at least one notch 36, 46 that is defined in the distal face 30B, 40B of the articular component. In some embodiments as the one shown in the figures, two such notches 36, 46 are provided, being diametrically opposed with respect to the assembly axis Z-Z. Each notch 36, 46 is designed to complementarily receive the projections(s) 27 of the platform upon the assembly between the platform and the articular component 30, 40, as shown for the articular component 30 in FIG. 5. When the platform 20 and the articular component 30, 40 are assembled together, the projection(s) 27 can interfere with the notch 36, 46 in an orthoradial direction with respect to the assembly axis Z-Z, that is to say in a direction that is orthogonal to a direction radial to the assembly axis Z-Z: in that way, the projection(s) 27 and the notch(es) 36, 46 interfere with each other to prevent rotation between the platform 20 and the articular component 30, 40 around the assembly axis Z-Z. In some embodiments as the one shown in the figures, the interference between the projection(s) 27 and the notch(es) 36, 46 prevents rotation between the platform 20 and the articular component 30, 40 in both directions of rotation around the assembly axis Z-Z; however, according to a variant not shown, rotation between the platform and the articular component may be prevented in one direction by dedicated projection(s) and notch(es), while being prevented in the opposed direction by other dedicated projection(s) and notch(es). In any case, the projection(s) 27 and the notch(es) 36, 46 respectively form rotation stop features of the platform 20 and of each of the articular components 30 and 40, these rotation stop features being designed to be engaged together and, when engaged together, to mechanically interfere with each other so as to prevent rotation between the platform and the articular component around the assembly axis Z-Z. In practice, the embodiments of these rotation stop features are not limitative, provided their engagement is operable intraoperatively, that is to say operable by a surgeon during surgery, i.e. in the course of a surgical procedure for implanting in a patient a glenoid implant from the set 1.

In some embodiments as the one shown for the articular component 30 in the FIGS. 1 to 5, the notch 36 of the articular component 30 may be not limited in the distal face 30B of the articular component 30 beforehand, that is to say before assembling this articular component with the platform 20. Indeed, when the material of the articular component 30 allows it, especially when the articular component is made of polymeric material, the notch(es) 36 may be directly cut into the articular component by the projection(s) 27 of the platform 20 upon the intraoperative assembly between the platform and the articular component 30 along the assembly axis Z-Z. That is the reason why in the FIGS. 1 and 3, the notches 36 of the articular component 30 are drawn only in dotted lines. In more detail, the articular component may be provided as a plastically deformable polymer, wherein the projections 27 can plastically deform the articular component to create the notches 36.

In any case, based on the foregoing, it will be understood that the aforesaid rotation stop features of the platform 20 and of the articular components 30 and 40 form at least partly a rotational connection for securing the platform with each of the articular components, this rotational connection being intraoperatively operable to prevent rotation between the platform and the articular component around the assembly axis Z-Z in both directions of rotation. This rotation connection is distinct from the aforesaid translational connection but is combined with this translational connection to form at least partly a platform-articular component attachment by which the platform 20 and each of the articular components 30 and 40 are secured together. This platform-articular component attachment is intraoperatively operable in the same way as the aforesaid platform-baseplate attachment is intraoperatively operable, but the platform-articular component attachment is independent from the platform-baseplate attachment, in the sense that the platform 20 is provided both to be secured to at least one of articular components 30 and 40 by the aforesaid platform-articular component attachment irrespective of its securement to the baseplate 10, and to be secured to the baseplate 10 by the aforesaid platform-baseplate attachment irrespective of its securement to the articular components 30 and 40. In other words, the securement of the platform 20 to each of the articular components 30 and 40 is dissociated from the securement of the platform to the baseplate 10.

In continuation of the above considerations, the order in which the platform-baseplate attachment and the platform-articular component attachment are respectively operated may be irrelevant, provided each of these two attachments can be operated without being troubled by the components assembled by the other attachment. That is the reason why in some embodiments as the one shown in the figures, each of the articular components 30 and 40 is provided with a through-hole 37, 47 at the proximal side of the articular components, this through-hole 37, 47 being coaxial with the through-hole 25 of the platform 20. In some embodiments as the one shown in the figures, the through-hole 37, 47 of the articular component 30, 40 is centered on the assembly axis Z-Z. A tool (not shown) can be introduced in the through-hole 37, 47 so as to actuate the locking member 50: even when the platform 20 is already assembled with one or the other of the articular components 30 and 40 by the aforesaid platform-articular component attachment, the platform-baseplate attachment can be operated so as to assembly the platform with the base plate 10.

The set 1 of the FIGS. 1 to 3 allows the surgeon to obtain two glenoid implants that differ from each other in their articular component, in the sense that the surgeon can obtain either the glenoid implant 2 of the FIGS. 4 and 5, by assembling the baseplate 10, the platform 20 and the articular component 30 together, or another glenoid implant (not shown) by assembling the baseplate 10, the platform 20 and the articular component 40 together. In other words, the various glenoid implants which can be obtained from the set 1 have in common the baseplate 10 and the platform 20. In that way, the inventories of prosthetic components that are required for obtaining the various glenoid implants are reduced, in the sense that the same baseplate 10 is usable with either of the various articular components 30 and 40, with the axial interposition of the same platform 20 between the baseplate and each of the articular components. It can also be underlined that even if using the platform 20 leads to divide the assembling link between the baseplate 10 and the articular component 30 or the baseplate 10 and the articular component 40 into both the platform-baseplate attachment and the platform-articular component attachment, the various glenoid implants that can be obtained from the set 1 are safe because all the degrees of freedom between the baseplate 10 and the platform 20 are blocked by the platform-baseplate attachment and all the degrees of freedom between the platform 20 and each of the articular components 30 and 40 are blocked by the platform-articular component attachment. At the same time, each of these two attachments is designed to be intraoperatively operated by the surgeon who can thus choose the articular component that is actually implanted among the two components 30 and 40 during surgery, i.e. in the course of the surgical procedure for implanting in a patient a glenoid implant from the set 1.

Of course, the articular components 30 and 40 which have been described so far are only examples of the wide variety of articular components which can be included in a set of prosthetic components, as the set 1 of the FIGS. 1 to 3. The FIGS. 6 and 7 give other examples of such other possible articular components.

Figure 6:
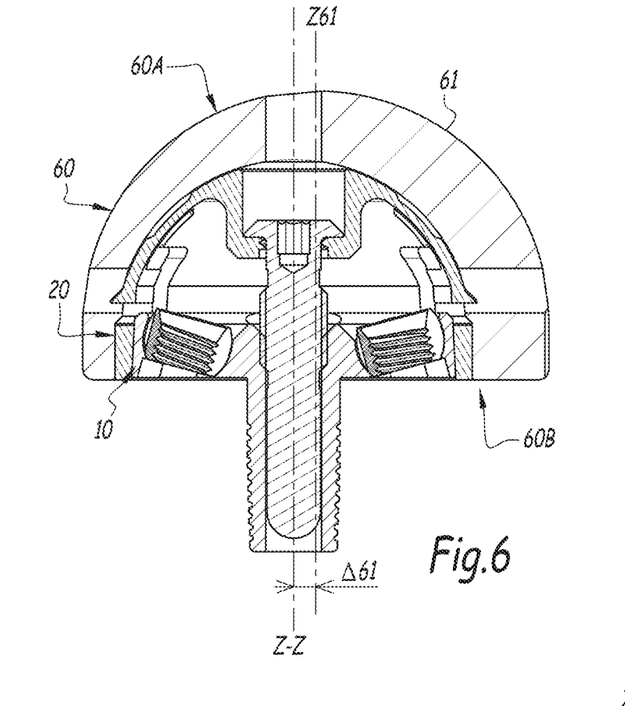
FIGS. 6 and 7 are views similar to FIG. 4, respectively illustrating other glenoid implants.

FIG. 6 shows an articular component 60, which has a distal face 60B that is similar to the distal face 30B, 40B of the articular component 30 or 40, but which has a proximal face 60A differing from the proximal faces 30A and 40A, in the sense that a convex articular surface 61 of this proximal face 60A defines a central axis Z61 that is parallel to the assembly axis Z-Z and laterally offset from this assembly axis with an offset value Δ61: this offset value Δ61 is different from the null offset value associated to the convex articular surfaces 31 and 41 which have respective central axes coinciding with the assembly axis Z-Z. In other words, the convex articular surface 61 is eccentric relative to the assembly axis Z-Z.

Figure 7:
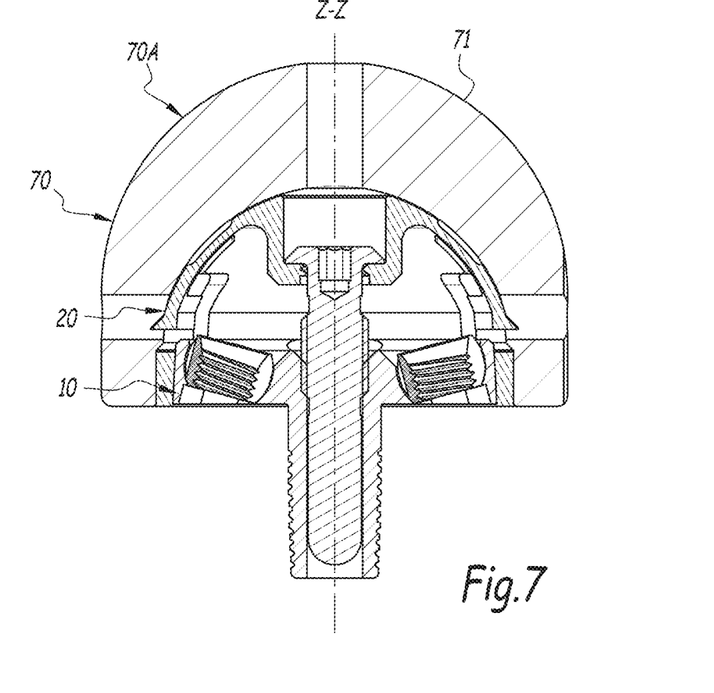

FIG. 7 shows an articular component 70 which differs from the articular components 30, 40 and 50 by the curvature of the convex articular surface 71 of its proximal face 70A.

According to other not-shown variants, each of the articular components 30, 40, 60 and 70 or at least one of these components is provided within the set 1 with at least two different sizes for their respective convex articular surface 31, 41, 61, 71, these various sizes being respectively adapted to various patient morphologies.

Based on the foregoing, it will be understood that more generally, the various articular components which can be included in the set 1 may differ from each other by at least one geometric feature of their respective convex articular surface. Of course, as indicated above, this differentiation between the various articular components may also be relative to the material compositions of each of the articular components, instead of or in addition to differentiation based on the geometry of the convex articular surfaces. In any case, the obtained glenoid implant is for a reversed shoulder prosthesis.

Figure 8:
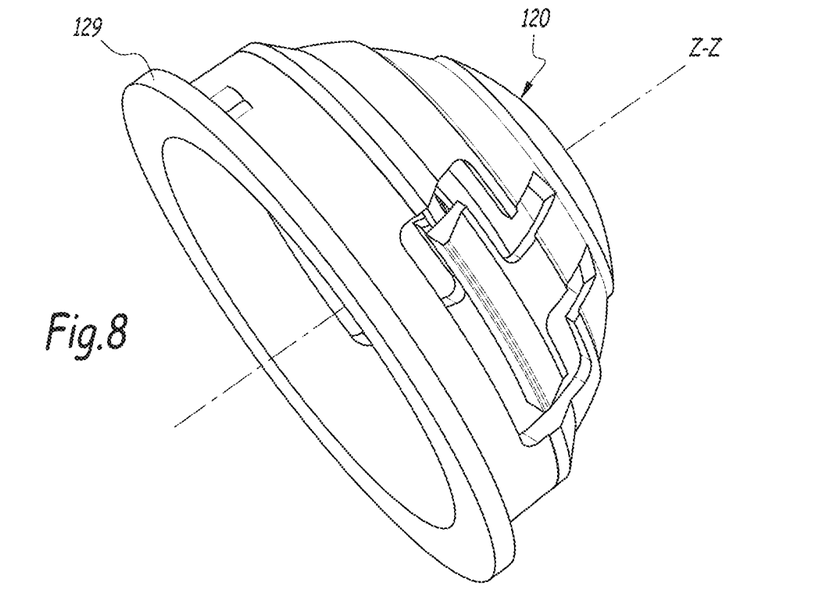
FIG. 8 is a perspective view of a variant for one of the components of the set of FIG. 1.
Figure 9:
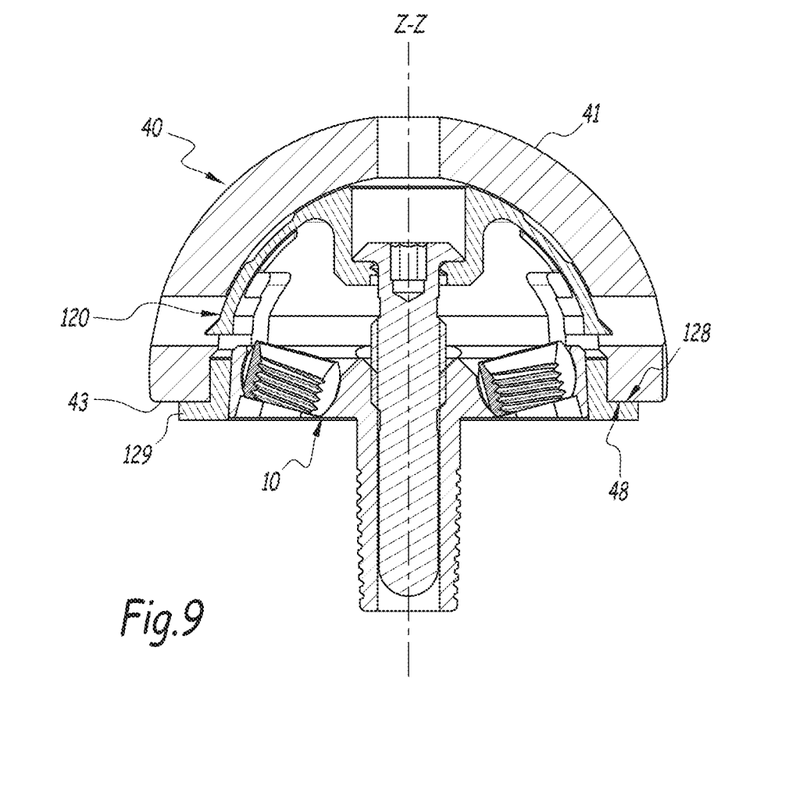
FIG. 9 is a view similar to FIG. 4, illustrating another glenoid implant including the component of FIG. 8.

Referring now to the FIGS. 8 and 9, a variant of the platform 20, which is labelled 120, is shown. The platform 120 is shown alone in FIG. 8, whereas it is shown assembled with the baseplate 10 and the articular component 40 in FIG. 9.

The platform 120 is similar to the platform 20, except with regard to the embodiment of their respective abutment surface. More precisely, contrary to the abutment surface 28 of the platform 20 that is defined by the top 21 and/or the walls 23.1 of the intermediate part 23 of the platform, the platform 120 has an abutment surface 128 which is defined by a collar 129, which radially projects outwardly from the distal base of the platform 120 and which runs around this base. The collar 129 is designed to be located against the edge 43 of the articular component 40 when the platform 120 and the articular components 40 are assembled together: in that way, the abutment surface 128 may be planar perpendicularly to the assembly axis Z-Z and is axially supported against the edge 43, more precisely against a bearing surface 48 thereof which is planar perpendicularly to the assembly axis Z-Z.

Engaging abutment and bearing surfaces which are planar, as the abutment surface 128 of the platform 120 and the bearing surface 48 of the edge 43 of the articular component 40, may be more appropriate than curved surfaces as the abutment surface 28 and the bearing surface 34, 44, in order to transmit significant forces between the platform 120 and the articular component 40 made of pyrocarbon along the assembly axis Z-Z in the axial direction in which the platform and the articular component move toward each other.

Figure 10:
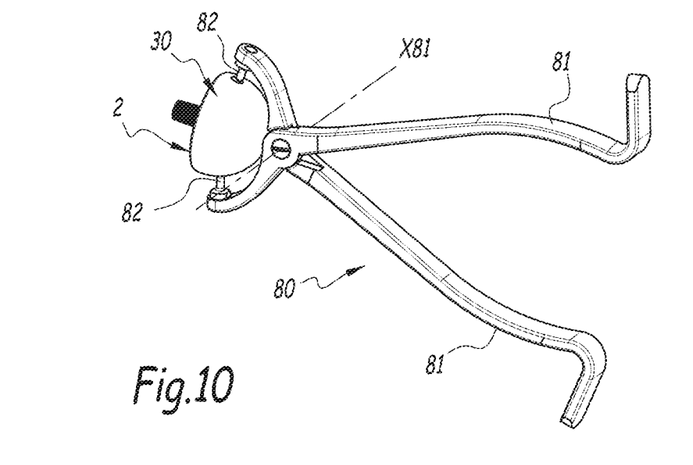
FIG. 10 is a perspective view of the glenoid implant of FIG. 4 and a tool for disassembling the glenoid implant.
Figure 11:
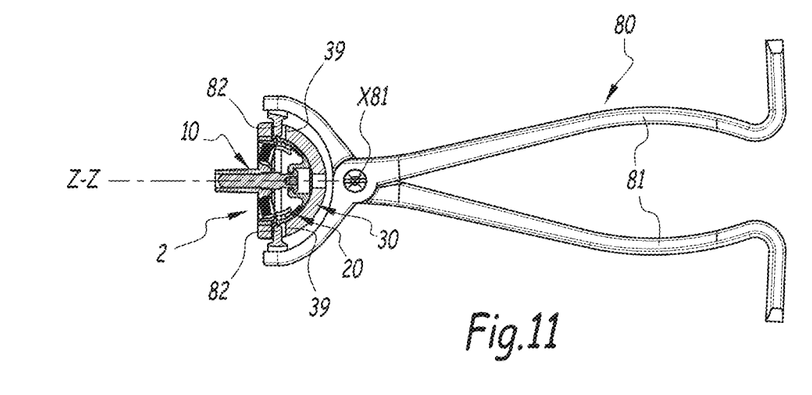
FIG. 11 is a view that is partly elevational and partly cross-sectional, illustrating the use of the tool of FIG. 10 for disassembling the glenoid implant of FIG. 4.

Referring now to the FIGS. 10 and 11, a tool 80 may be optionally added to the set 1. This tool 80 is adapted to counteract the platform-articular component attachment in a glenoid implant obtained from the prosthetic components of the set 1. In the example shown in the FIGS. 10 and 11, the tool 80 is considered in combination with the glenoid implant 2 of the FIGS. 4 and 5.

The tool 80 comprises two branches or handles 81 which articulate with respect to the one around an axis X81. When the tool is in use, the axis X81 is perpendicular to the assembly axis Z-Z. At one of its ends, each branch 81 is provided with a pin 82. The two pins 82 come together and move apart when the branches 81 articulate one with respect to the other about the axis X81. Each pin 82 is designed to be introduced into a through-hole 39 of the articular component 30 of the glenoid implant 2: as shown in the FIGS. 1 to 4, the two corresponding through-holes 39 of the articular component 30 are diametrically opposed with respect to the assembly axis Z-Z and are aligned in a direction radial to the assembly axis Z-Z. Furthermore, when the platform and the articular component 30 are assembled together, the through-holes 39 respectively open on the flanges 23.2. In that way, by introducing the pins 82 into the through-holes 39, the pins 82 can be moved toward each other so as to contact the flanges 23.2 respectively, as shown in FIG. 11. By further moving the pins 82, the pins pinch the flanges 23.2 so as to deform them from their rest position to their deformed position: the projections 26 of the flanges 23.2 do not interfere anymore with the recess 35, so that the articular component 30 can be moved away from the platform 20 along the assembly axis Z-Z. The articular component 30 is thus disassembled from the platform 20.

Of course, the tool 80 may be used on any of the articular components of the set 1, provided these articular components are provided with through-holes similar to the through-holes 39 of the articular component 30. Such through-holes are thus provided in the articular component 40, as shown in the FIGS. 1 to 3, in the articular component 60, as shown in FIG. 6, and in the articular component 70, as shown in FIG. 7. It will also be understood that such through-holes may be used by the surgeon to counteract the platform-articular component attachment by means of any appropriate tool which is designed to act on the platform 20 or 120 in the same way as the tool 80.

The invention claimed is:
1. Glenoid implant for a shoulder prosthesis, comprising:
   a baseplate,
   an articular component which has a convex articular surface, and
   a platform which is provided both to be secured to the articular component by a first attachment and to be secured to the baseplate by a second attachment, the first attachment being independent from the second attachment,
   wherein the first attachment defines an assembly axis which extends in a proximodistal direction and along which the platform and the articular component are assembled together,
   and wherein the first attachment comprises:
      a translational connection that is intraoperatively operable to prevent translation between the platform and the articular component along the assembly axis, and a rotational connection that is intraoperatively operable to prevent rotation between the platform and the articular component around the assembly axis,
the translational connection and the rotational connection being distinct from each other, wherein the translational connection includes at least one translational stop feature of the platform and at least one translational stop feature of the articular component, which are designed to be intraoperatively engaged together and, when engaged together, to mechanically interfere with each other so as to prevent translation between the platform and the articular component along the assembly axis,
wherein the at least one translational stop feature of the articular component comprises at least one recess,
wherein the at least one translational stop feature of the platform comprises at least one flange that is elastically deformable with respect to the rest of the platform between:
a rest position, in which the at least one flange is snapped into and interferes with the at least one recess to prevent translation along the assembly axis in an axial direction in which the platform and the articular component move away from each other when the platform and the articular component are assembled together, and
a deformed position, in which the at least one flange does not interfere with the at least one recess,
wherein the at least one flange is elastically deformable upon intraoperative assembly between the platform and the articular component from the rest position to the deformed position by pinching the at least one flange toward the assembly axis and from the deformed position to the rest position by elastic return, and
wherein the articular component has at least one through-hole, which opens on the at least one flange when the platform and the articular component are assembled together and into which a tool is insertable to act on the at least one flange to deform the at least one flange from the rest position to the deformed position.

2. Glenoid implant according to claim 1, wherein the platform has a dome shape that is centered on the assembly axis, so that the platform has a convex proximal face and a concave distal face which are both centered on the assembly axis, and wherein the platform comprises a proximal top, a distal base and an intermediate part between the proximal top and the distal base, the intermediate part including:
at least one wall which is curved and rigidly connects the proximal top and the distal base, and
the at least one flange,
the at least one wall and the at least one flange being arranged in turn around the assembly axis.

3. Glenoid implant according to claim 2, wherein the at least one flange in the rest position has a curvature that is identical to the curvature of the at least one wall.

4. Glenoid implant according to claim 2, wherein the articular component has a proximal face, which is at least partly convex and includes the convex articular surface, and a distal face, which is at least partly concave and includes a socket, which is linked to the convex articular surface by an edge of the articular component and which is provided internally with the at least one recess, a part of the platform being housed within the socket when the platform and the articular component are assembled together.

5. Glenoid implant according to claim 4, wherein the at least one translational stop feature of the platform further comprises at least one abutment surface, and wherein the at least one translational stop feature of the articular component further comprises at least one bearing surface which is axially supported against the at least one abutment surface to prevent translation along the assembly axis in an axial direction in which the platform and the articular component move toward each other.

6. Glenoid implant according to claim 5, wherein the at least one bearing surface of the articular component is concave and is defined into the socket, and wherein the at least one abutment surface of the platform is convex and is defined by the part of the platform, which is housed within the socket when the platform and the articular component are assembled together.

7. Glenoid implant according to claim 5, wherein the at least one bearing surface of the articular component is planar perpendicularly to the assembly axis and is defined by the edge of the articular component, and wherein the at least one abutment surface of the platform is planar perpendicularly to the assembly axis and is defined by a collar of the platform, the collar being located against the edge of the articular component when the platform and the articular component are assembled together.

8. Glenoid implant according claim 4, wherein the rotational connection includes at least one rotation stop feature of the platform and at least one rotation stop feature of the articular component, which are designed to be intraoperatively engaged together and, when engaged together, to mechanically interfere with each other so as to prevent rotation between the platform and the articular component around the assembly axis, wherein the at least one rotation stop feature of the platform comprises at least one projection that is provided on the convex proximal face of the platform, the at least one projection being designed to project from the rest of the convex proximal face of the platform and being arranged radially to the assembly axis, and wherein the at least one rotation stop feature of the articular component comprises at least one notch, which is defined in the socket and with which the at least one projection orthoradially interferes to prevent rotation around the assembly axis.

9. Glenoid implant according to claim 8, wherein the at least one projection and the at least one notch are designed to interfere together to prevent rotation around the assembly axis in both directions of rotation.

10. Glenoid implant according to claim 8, wherein the at least one notch is cut into the articular component by the at least one projection upon intraoperative assembly between the platform and the articular component.

11. Glenoid implant according to claim 1, wherein the second attachment comprises:
a taper connection between the platform and the baseplate, and
a locking member extending between the platform and the baseplate,
the taper connection and the locking member being intraoperatively operable to fixedly secure the platform and the baseplate together.

12. Glenoid implant according to claim 6, wherein the part of the platform, which defines the at least one abutment surface and which is housed within the socket when the platform and the articular component are assembled together, includes the proximal top or the at least one wall of the intermediate part.

13. Glenoid implant according to claim 8, wherein the at least one projection is carried by the at least one wall of the intermediate part.

14. Set for assembling a glenoid implant, comprising:
a glenoid implant for a shoulder prosthesis, comprising:
  a baseplate,
  an articular component which has a convex articular surface, and
  a platform which is provided both to be secured to the articular component by a first attachment and to be secured to the baseplate by a second attachment, the first attachment being independent from the second attachment,
wherein the first attachment defines an assembly axis which extends in a proximodistal direction and along which the platform and the articular component are assembled together,
and wherein the first attachment comprises:
  a translational connection that is intraoperatively operable to prevent translation between the platform and the articular component along the assembly axis, and
  a rotational connection that is intraoperatively operable to prevent rotation between the platform and the articular component around the assembly axis,
the translational connection and the rotational connection being distinct from each other, wherein the translational connection includes at least one translational stop feature of the platform and at least one translational stop feature of the articular component, which are designed to be intraoperatively engaged together and, when engaged together, to mechanically interfere with each other so as to prevent translation between the platform and the articular component along the assembly axis,
wherein the at least one translational stop feature of the articular component comprises at least one recess,
wherein the at least one translational stop feature of the platform comprises at least one flange that is elastically deformable with respect to the rest of the platform between:
  a rest position, in which the at least one flange is snapped into and interferes with the at least one recess to prevent translation along the assembly axis in an axial direction in which the platform and the articular component move away from each other when the platform and the articular component are assembled together, and
  a deformed position, in which the at least one flange does not interfere with the at least one recess,
wherein the at least one flange is elastically deformable upon intraoperative assembly between the platform and the articular component from the rest position to the deformed position by pinching the at least one flange toward the assembly axis and from the deformed position to the rest position by elastic return, and
wherein the articular component has at least one through-hole, which opens on the at least one flange when the platform and the articular component are assembled together and into which a tool is insertable to act on the at least one flange to deform the at least one flange from the rest position to the deformed position;
  at least one other articular component such that the set comprises at least two articular components, each of the at least two articular components being configured to be assembled with the platform so as to be the articular component of the glenoid implant,
wherein the platform is assembled selectively with the at least two articular components along the assembly axis.

15. Set according to claim 14, wherein the set further comprises a tool for counteracting the first attachment between the platform and at least one of the at least two articular components, the tool being designed to be introduced into the at least one through-hole and to act on the at least one flange to deform the at least one flange from the rest position to the deformed position.

16. Set according to claim 14, wherein the at least two articular components are made in respective material compositions which are different.

17. Set according to claim 16, wherein each of the material compositions is selected from a group including a polymeric material, a metal material and a ceramic.

18. Set according to claim 14, wherein the at least two articular components differ from each other by at least one geometric feature of respective convex articular surface thereof.

19. Set according to claim 18, wherein each of the respective convex articular surfaces of the at least two articular components defines a central axis which, when the corresponding articular component of the at least two articular components is assembled with the platform, is both parallel to the assembly axis and laterally offset from the assembly axis with an offset value that is possibly null, and wherein the offset values respectively associated to the at least two articular components are different.

* * * * *